US00PP20616P2

(12) United States Plant Patent
Jandrew

(10) Patent No.: US PP20,616 P2
(45) Date of Patent: Dec. 29, 2009

(54) *IPOMOEA* PLANT NAMED 'SEKI LIM'

(50) Latin Name: *Ipomoea batatas L. Lam*
Varietal Denomination: Seki Lim

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,553

(22) Filed: Dec. 12, 2008

(51) Int. Cl.
*A01H 5/00* (2006.01)

(52) U.S. Cl. ..... Plt./258

(58) Field of Classification Search ..... Plt./258
See application file for complete search history.

*Primary Examiner*—Kent L Bell
(74) *Attorney, Agent, or Firm*—S. Matthew Edwards

(57) ABSTRACT

A new *Ipomoea* plant named 'Seki Lim' particularly distinguished by compact and mounding plant habit that becomes more outwardly trailing with age, vigorous, freely branching with dense lime-green, heart shaped to slightly palmately-lobed foliage, with soft purple and white flowers.

1 Drawing Sheet

Latin name of the genus and species of the plant claimed: *Ipomoea batatas* (*L.*) *Lam.*

Varietal denomination: 'Seki Lim'.

BACKGROUND OF THE NEW PLANT

The present invention comprises a new *Ipomoea*, botanically known as *Ipomoea batatas* (*L.*) *Lam*, and commonly known as Ornamental Sweet Potato, and hereinafter referred to by the variety name 'Seki Lim'. These plants are grown, not for their flowers, but for their foliage and plant habit characteristics. These plants flower very rarely and then only under strict short day lengths. Each flower is ephemeral, in that it only lasts up to 24 hours, and blooms mostly through the night and early morning hours.

'Seki Lim' is a product of a planned breeding program. The new cultivar 'Seki Lim' has a compact and mounding plant habit that becomes more outwardly trailing with age, vigorous, freely branching with dense lime-green heart shaped to slightly palmately-lobed foliage, with soft purple and white flowers.

'Seki Lim' originated from a cross pollination in a controlled breeding program in Gilroy, Calif. USA. The female parent was 'Sweet Caroline Light Green' (U.S. Plant Pat. No. 15,028). 'Sweet Caroline Light Green' has lighter green foliage, a less compact habit, longer petioles and darker flower color than 'Seki Lim'.

The male parent of 'Seki Lim' was 'Margurite', an unpatented commercial variety, with larger foliage and less compact plant habit than 'Seki Lim'.

'Seki Lim' was selected as one flowering plant within the progeny of the stated cross in March 2007, in a controlled environment in Gilroy, Calif. USA. The pollination took place in October 2006 and the seed sown in December 2006.

The first act of asexual reproduction of 'Seki Lim' was accomplished when vegetative cuttings were used from the initial selection in the March 2007 in a controlled environment in Gilroy, Calif. USA.

Horticultural examination of plants grown from cuttings of the plant initiated in March 2007 in Gilroy, Calif. USA, and continuing thereafter, has demonstrated that the combination of characteristics as herein disclosed for 'Seki Lim' are firmly fixed and are retained through successive generations of asexual reproduction.

'Seki Lim' has not been observed under all possible environmental conditions. The phenotype may vary significantly with variations in environment such as temperature, light intensity and day length.

A Plant Breeder's Right for this cultivar was applied for in Canada on Dec. 24, 2007. 'Seki Lim' has not been made publicly available more than one year prior to the filing of this application.

DESCRIPTION OF DRAWING

The accompanying photographic drawing shows typical foliage and plant habit characteristics of 'Seki Lim' with colors being as true as possible with an illustration of this type. The photographic drawing shows 3 young potted plants of the new variety growing in a 10 inch container. These plants were grown and photographed in Gilroy, Calif. USA in April of 2008.

DETAILED BOTANICAL DESCRIPTION

The measurements were taken in October 2008 in Gilroy, Calif. USA on plants that were growing in 6 inch pots in a greenhouse. Culture of these plants started in about August 2008, when they came from sterile tissue culture tubes after laboratory micropropagation.

Color chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Ipomoea* as a new and distinct variety.

TABLE 1

DIFFERENCES BETWEEN THE NEW VARIETY 'SEKI LIM' AND A SIMILAR VARIETY

| | 'Seki Lim' | 'Sweet Caroline Sweetheart Light Green' (U.S. Plant Pat. No. 18,572) |
|---|---|---|
| Foliage shape | Slightly more palmately lobed | Less lobed, more cordate |
| Foliage size | Larger | Smaller |
| Petiole size | Longer | Shorter |
| Stem color | RHS 146B | RHS 145B |

Plant:

*Form, growth and habit.*—Compact and mounding plant habit that becomes more outwardly trailing with age, freely branching with dense foliage, vigorous.

*Plant height.*—13–16 cm.

*Plant width.*—40–45 cm.

Roots/tubers:

*Type.*—At the age of these plants used for the descriptive data, there were no real tubers forming. The roots themselves are thick, fleshy and cream to white.

Foliage:

*Type.*—Alternate, simple.

*Immature, leaf color, upper surface.*—Between RHS N144A and RHS 144A; RHS 166A anthocyanins at the margins.

*Lower surface.*—Closest to RHS 146C.

*Mature, leaf color, upper surface.*—Closest to RHS 144A; RHS 166A at the margins.

*Lower surface.*—Closest to RHS 146D.

*Length.*—11.5–13.4 cm.

*Width.*—10.4–12.5 cm.

*Shape.*—Roughly cordate to deltoid; slightly palmate, 3 lobed.

*Base shape.*—Cordate.

*Apex shape.*—Apiculate to aristate.

*Margin.*—Entire.

*Texture.*—Hirsute on the margins of both surfaces.

*Color of veins, upper surface.*—RHS 144C; RHS 187A but a little more grey, mid vein basally.

*Color of veins, lower surface.*—RHS144C; RHS 187A but a little more grey, mid vein basally.

*Petioles color.*—RHS 144B.

*Petioles length.*—8.3–9.0 cm.

*Diameter of petiole.*—0.3 cm.

*Texture.*—Glabrous.

Stem:

*Color of stem.*—RHS 146B.

*Length of stem.*—25–35 cm.

*Diameter.*—0.4–0.5 cm.

*Length of internodes.*—1.0–3.5 cm.

*Texture.*—Glabrous.

Inflorescence:

*Type.*—Ephemeral; rarely see many flowers. Flowers only under very strict short day lengths.

*Fragrance.*—None.

*Color of peduncle.*—RHS 144A but slightly lighter.

*Length of peduncle.*—0.3–0.4 cm.

*Peduncle diameter.*—0.2 cm.

*Texture.*—Glabrous.

Corolla:

*Form.*—Single trumpet-shaped flowers arise from leaf axils comprised of 5 petals fused at the corolla length and base.

*Flower diameter.*—4.0–4.5 cm.

*Flower depth.*—3.0–3.5 cm.

*Color of petals, upper surface.*—RHS 75D; RHS 76C at the margins; RHS 77C mid veins.

*Color of petals, lower surface.*—RHS 76D; RHS 77D mid veins.

*Length of petals.*—1.5–1.6 cm.

*Width of petals.*—1.4–1.5 cm.

*Petal shape.*—Obovate.

*Apex shape.*—Broadly obtuse to rounded.

*Margin.*—Entire.

*Petal texture.*—Papillose on upper surface and glabrous on the under surface.

*Corolla color inner surface.*—Between RHS 77A and 77B; RHS 77A veins.

*Outer surface.*—RHS 77C but greyer.

*Corolla diameter at flare.*—1.6–2.0 cm.

Bud (just before opening):

*Color.*—RHS 63B.

*Length.*—1.5 cm.

*Width.*—0.4–0.5 cm.

*Shape.*—Orbicular.

*Calyx.*—5 sepals fused at the base.

*Color of sepals, inner surface.*—Closest to RHS 148A.

*Outer surface.*—Closest to RHS 148A.

*Length of sepals.*—0.7–0.8 cm.

*Width of sepals.*—0.2–0.3 cm.

*Sepal shape.*—Lanceolate.

*Apex shape.*—Acute.

*Margins.*—Entire.

*Texture.*—Slightly pubescent on the outer surface and glabrous on the inner surface.

Reproductive organs:

*Pistil.*—1.

*Length.*—2–2.3 cm.

*Style color.*—RHS N155B but whiter.

*Style length.*—1.7–2.0 cm.

*Stigma color.*—RHS N155B but whiter.

*Stamens.*—5.

*Color of filaments.*—RHS N155B but whiter.

*Length filaments.*—0.5–0.6 cm.

*Anther color.*—RHS 155C.

*Length of anthers.*—0.2–0.3 cm.

*Color of pollen.*—RHS 155A.

*Pollen amount.*—Scarce.

*Fertility/seed set.*—Not observed on this hybrid.

Disease/pest resistance: Disease resistance or susceptibility has not been observed on this hybrid.

What is claimed is:

1. A new and distinct variety of *Ipomoea* plant named 'Seki Lim', substantially as illustrated and described herein.

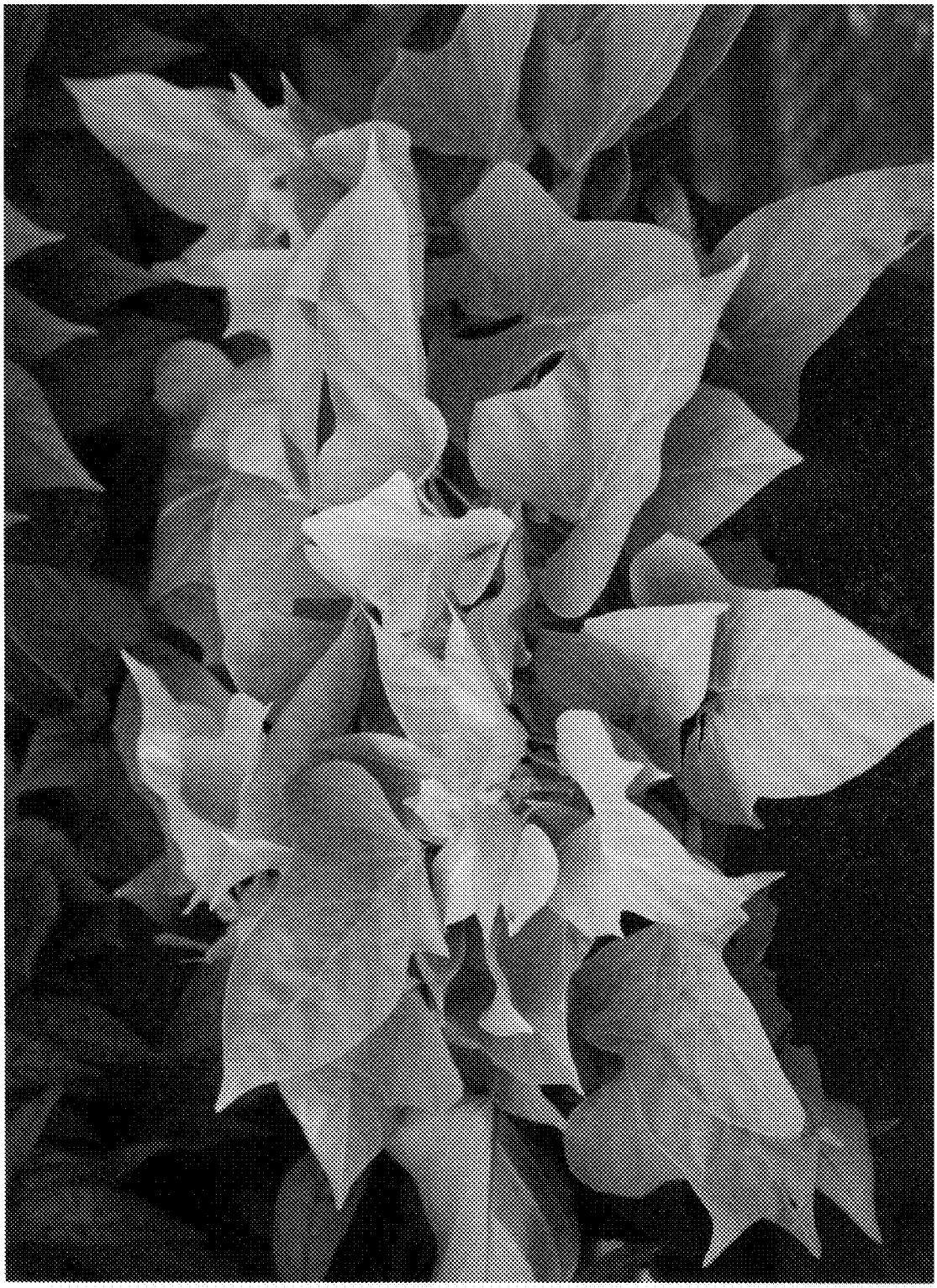

* * * * *